US005537996A

United States Patent [19]
McPhee

[11] Patent Number: 5,537,996
[45] Date of Patent: Jul. 23, 1996

[54] HEATED RESPIRATORY HUMIDIFIER CONDUIT

[75] Inventor: Stephen W. McPhee, Auckland, New Zealand

[73] Assignee: Fisher & Paykel Limited, Auckland, New Zealand

[21] Appl. No.: 343,727

[22] Filed: Nov. 22, 1994

[30] Foreign Application Priority Data

Nov. 22, 1993 [NZ] New Zealand .......................... 250248

[51] Int. Cl.⁶ .................................................. A61M 16/16
[52] U.S. Cl. ...................... 128/204.17; 392/398; 392/401
[58] Field of Search ................... 128/204.17; 392/397, 392/398, 470, 401, 488, 486; 122/4 H, 13.1

[56] References Cited

U.S. PATENT DOCUMENTS

| | | | |
|---|---|---|---|
| 3,249,108 | 5/1966 | Terman | 128/204.17 |
| 4,922,901 | 5/1990 | Brooks et al. | 128/204.17 |
| 5,392,770 | 2/1995 | Clawson et al. | 128/204.17 |

FOREIGN PATENT DOCUMENTS 02566 5/1986 WIPO .................................. 128/204.17

Primary Examiner—Edgar S. Burr
Assistant Examiner—William J. Deane, Jr.
Attorney, Agent, or Firm—Trexler, Bushnell, Giangiorgi & Blackstone, Ltd.

[57] ABSTRACT

A heated respiratory humidifier conduit for use with a respiratory humidifier/ventilator circuit. The conduit consists of an inspiratory tube passing gases from the humidifier/ventilator to the patient and an expiratory tube passing exhaled gases from the patient back to the gases supply. An insulated resistance heating wire runs the full length of the inspiratory tube to reduce condensation forming on the walls of the tube. The return path for the heating wire is supplied by an insulated conductor which also runs the full length of the inspiratory tube and is connected to the heating wire near the patient. This ensures that the voltage of the heating wire is substantially zero volts at the patient end of the conduit, minimizing the interactions with other patient connected equipment.

8 Claims, 1 Drawing Sheet

HEATED RESPIRATORY HUMIDIFIER CONDUIT

BACKGROUND OF THE INVENTION

1. Field of the Invention

This invention relates to respiratory humidifiers and more particularly but not solely to respiratory humidifier conduits used in the breathing circuits of humidifiers to provide humidified gases to a patient or other person in need of such gases.

2. Description of the Prior Art

In order to supply gases, for example humidified gases, to a patient or other person in need of such gases, flexible conduits have been used both from the gases supply to the patient (inspiratory conduit) and from the patient back to the gases supply (expiratory gases). When the supplied gas is a humidified gas, it is desirable to minimise the amount of condensation occurring on the inner walls of the conduit as this condensation soon accumulates requiring regular draining. Some existing respiratory humidifier conduits incorporate heating wires in an attempt to reduce condensation and also to assist in the control of the temperature of the humidified gases within the conduit being delivered to the patient.

An example of a respiratory humidifier conduit incorporating a heating wire is disclosed in our prior U.S. Pat. No. 4,708,831 to Elsworth et al. The heating wire disclosed is a looped heating element with the two free ends of the loop emerging from the conduit for connection to a source of alternating voltage on the humidifier. Voltage is applied across the ends of the heating wire and, as the heating wire is looped, the voltage at the point closest to the patient has reduced to around half the input voltage. It has been found that, in some medical applications where sensitive monitoring equipment is positioned on the patient, although the voltage at the point closest to the patient is very low (for example $11V_{rms}$), the electric field produced from the heater wire can, in some instances, be registered by the monitoring devices. It has been found that this is usually an intermittent problem and is dependent on many factors, such as the frequency of the heating wire voltage and the sensitivity and quality of the medical monitoring device and connections thereto.

BRIEF SUMMARY OF THE INVENTION

It is, therefore, an object of the present invention to provide a heated respiratory conduit which goes some way towards overcoming the above disadvantages or which will at least provide the public with a useful choice.

In one aspect the invention consists in a heated respiratory conduit for use with a respiratory humidifier/ventilator circuit comprising:

a tube having couplings at a patient and an equipment end respectively, an insulated resistance heater wire contained within the tube running substantially the full length of the tube, a low resistance insulated resistance return wire contained within the tube running substantially the full length of the tube, said resistance heater wire and said return wire each being terminated at the equipment end to respective electrical connectors and being connected together at the patient end.

In a second aspect, the invention consists in a heated respiratory conduit adapted to receive and channel gases from a humidification device comprising:

a conduit having a connection means at its distal end for connection to said humidification device to receive said gases, heating element means within said conduit extending along the length of said conduit, low resistance electrical conducting means within said conduit extending along the length of said conduit, said heating element means and said low resistance electrical conducting means being connected together at their proximal ends.

The invention consists in the foregoing and also envisages constructions of which the following gives examples.

BRIEF DESCRIPTION OF THE DRAWINGS

One preferred form of the present invention will now be described with reference to the accompanying drawings in which.

DETAILED DESCRIPTION OF THE PREFERRED EMBODIMENT

Figure 1:
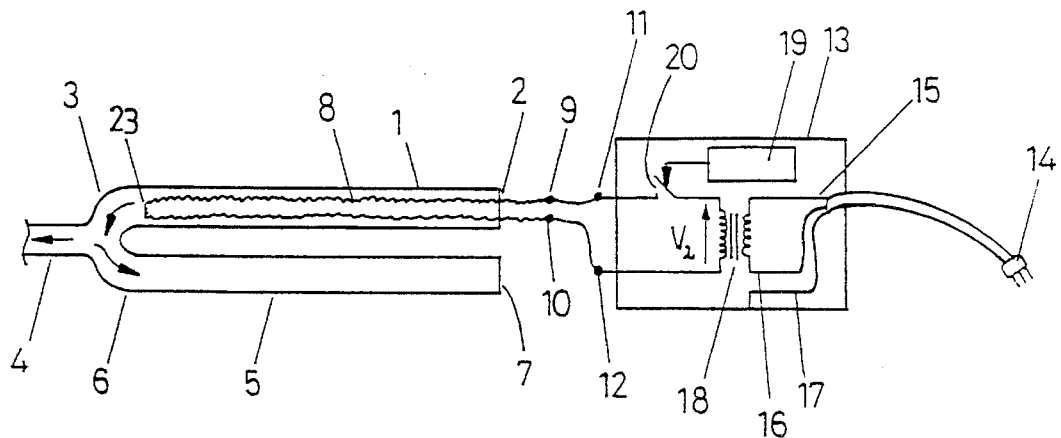
FIG. 1 is a basic schematic diagram of a heated humidified conduit system according to the prior art.

A respiratory humidifier conduit enables gases (for example, humidified gases) to be transported from a gases supply (such as a humidifier or ventilator) to a patient or other person in need of such gases. A prior art heated respiratory humidifier conduit is shown in FIG. 1. The humidifier conduit (as shown in FIG. 1) ordinarily comprises an inspiratory tube 1 connected at its distal end 2 to the gases outlet of a respiratory humidifier (not shown) and at its proximal end 3 to a "Y" shaped connector having three inlet/outlet ports. One port 4 of the "Y" shaped connector directs the inspiratory gases to the patient and also receives exhaled air from the patient. The expired air is channelled by the "Y" shaped connector to an expiratory tube 5 via the third port 6 of the "Y" shaped connector so that the expiratory gases may be returned to the humidifier/ventilator (not shown) from the end 7 of the expiratory tube 5.

As the gases being transported by the conduit are heated and humidified, and thus laden with water vapour, condensation will occur at any point along the inner wall of the conduit where the surface temperature of the conduit is lower than the temperature of the gases. This undesirable occurrence leads to a build up of liquid water within the conduit which must be regularly drained in order that the patient is not provided with liquid water. In an effort to overcome this disadvantage, insulated heater wire 8 is provided within the inspiratory gases tube and is commonly made from a wound tin alloy. It can be seen from FIG. 1 that the heater wire 8 is looped, having both ends 9 and 10 protruding from the end 2 of the inspiratory tube and having a bend 23 approximately half way along the heater wire 8, bend 23 being the closest point that the heater wire comes to the "Y" shaped connector. The ends of the heater wire 9 and 10 are connected to respective outputs 11 and 12 of a power supply 13 which is usually supplied within the humidifier (not shown). The terminals 11 and 12 ordinarily available on a humidifier for convenient connection of the heater wire.

Power is supplied to the humidifier via standard domestic or industrial supply (for example 230–240 volts AC) via plug 14 so that phase 15, neutral 16 and earth 17 conductors are available within the humidifier. The earth conductor is connected to the metal chassis of the humidifier while the heater wire 8 is supplied with power from the secondary side of a step down transformer 18 which is connected to the external voltage supply across the phase 15 and neutral 16 conductors. A controller 19, within the humidifier, controls a switch 20 which, when closed, energises the heater wire. The controller 19 may respond to inputs from temperature sensors (not shown) at various positions within the humidifier conduit or external of the conduit as well as receiving instructions from, for example, a further controller within the humidifier which controls the overall operation of the humidifier. The secondary voltage $V_2$ of transformer 18 is stepped down to around 22 volts RMS and at the same frequency as the supply (that is, 50 or 60 hertz). It can thus be seen that at point 23 on the heater wire the voltage will be approximately half the transformer secondary voltage, for example 11 volts RMS.

Figure 2:
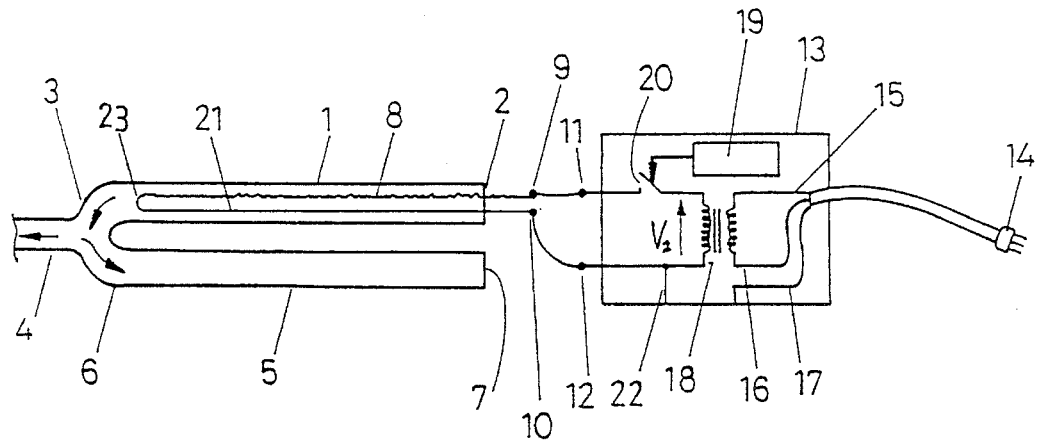
FIG. 2 is a basic schematic diagram of the heated respiratory humidified conduit system of the present invention.
Figure 3:
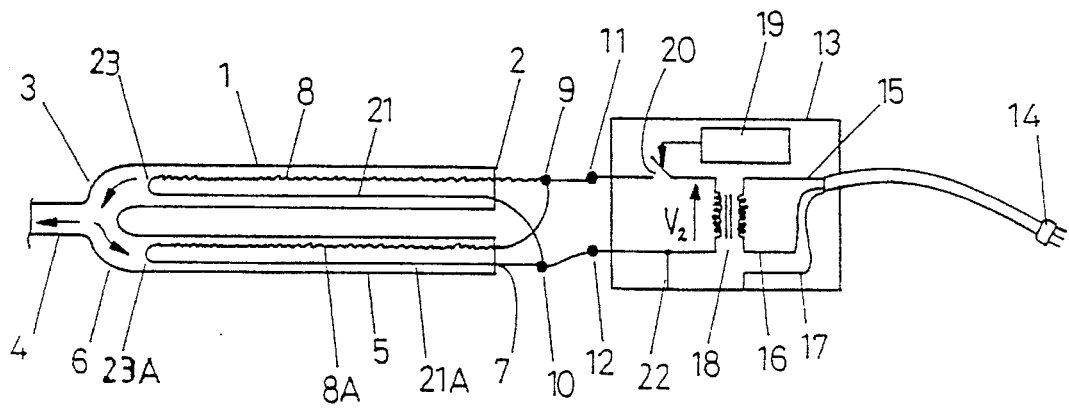
FIG. 3 is a basic schematic diagram of an alternate preferred embodiment of the heated respiratory humidified conduit system of FIG. 2.

With reference now to FIGS. 2 and 3, each of the features common to FIG. 1 are referenced with the same reference numerals.

FIG. 2 shows a preferred embodiment of the present invention in which the heater wire 8 is now a single length and approximately half the length of the heater wire shown in FIG. 1. The heater wire 8 in FIG. 1 extends from connection 9, along the inspiratory tube 1 to close to "Y" shaped connector 4. At end 23 of the heater wire 8 a connection is made to a low resistance insulated return wire 21 which travels back along the inspiratory tube to connection 10. Thus, the arrangement shown in FIG. 2 for the heater wire is retro-fitable to existing humidifiers in that the same external connections are made to the humidifier. In addition, by ensuring that the resistance of the heater wire of FIG. 2 is double the resistance per unit length of the heater wire shown in FIG. 1, the power and current requirements of the heater wire in FIG. 2 are substantially the same as the heater wire configuration shown in FIG. 1. Also, this new configuration has the advantage that at point 23, at the point on the heater wire closest to the patient, the voltage is very nearly 0 volts as earth return 21 is connected to the chassis of the humidifier via conductor 22 which is connected to ground.

In an alternative preferred embodiment of the present invention, FIG. 3 shows the respiratory humidified conduit having separate heater wires within the inspiratory and expiratory tubes. Heater wire 8 is within the inspiratory tube 1 while a second heater wire 8A is within the expiratory tube 5. This arrangement attempts to reduce the amount of condensation occurring in the expiratory tube, as well as the inspiratory tube, to reduce the draining required from the conduit. In order to arrange that the ends 23 and 23A of the respective heater wires are both at or around 0 volts potential, the two heater wires are configured in parallel such that the second heater wire 8A shares connection 9 with the first heater wire 8 and is connected at point 23A to the second earth return conductor 21A which extends from point 23A to connection 10. It can therefore be seen that the arrangement shown in FIG. 3 is also retro-fitable to a standard humidifier as it shares common connections with existing humidifiers and by choosing the appropriate resistance wire, the power requirements of the heater wire can be matched to existing transformers.

From the foregoing it can be seen that the present invention has the desirable property that the voltage of the heater wire at the point closest to the patient is substantially 0 volts. This has been found to be desirable in cases where the patient receiving the gases from the humidifier conduit is receiving medical attention including monitoring by devices sensitive to electric fields, for example, Electrocardiograph machines (ECG). As the sensors for ECG's are placed on the chest of the patient or in positions close to the humidifier conduit heater wire, it is desirable that the fields generated close to the sensors by the heater wire be as low as possible and this is achieved by the present invention. It can thus be seen that the present invention provides a simple, yet effective, answer to the problem of electric field coupling to sensitive monitoring devices which is also easily retrofitable to currently available humidification apparatus.

We claim:

1. A heated respiratory conduit for use with a respiratory humidifier/ventilator circuit comprising:

a tube having couplings at a patient end and an equipment end respectively, an insulated resistance heater wire contained within the tube running substantially the full length of the tube, a low resistance insulated return wire contained within the tube running substantially the full length of the tube, said resistance heater wire and said return wire each being terminated at the equipment end to respective electrical connectors and being connected together at the patient end.

2. A heated respiratory conduit as claimed in claim 1 further comprising an inspiratory tube, to direct gases from said, respiratory humidifier, connected to an expiratory tube, to return gases to the humidification device, and an outlet for said gases between said inspiratory and expiratory tubes.

3. A heated respiratory conduit as claimed in claim 2 wherein said resistance heater wire and said return wire substantially extend the length of said inspiratory tube.

4. A heated respiratory conduit as claimed in claim 2 wherein a second resistance heater wire is provided within said expiratory tube and extends substantially the full length of said expiratory tube, and a second return wire is provided within said expiratory tube, extending substantially the full length of said expiratory tube and connected at said patient end to said second resistance heater wire.

5. A heated respiratory conduit adapted to receive and channel gases from a humidification device comprising:

a conduit having a connection means at its distal end for connection to said humidification device to receive said gases, heating element means within said conduit extending along the length of said conduit, low resistance electrical conducting means within said conduit extending along the length of said conduit, said heating element means and said low resistance electrical conducting means being connected together at their proximal ends.

6. A heated respiratory conduit as claimed in claim 5 further comprising an inspiratory tube, to direct gases from said humidification device, connected to an expiratory tube, to return gases to the humidification device, and an outlet for said gases between said inspiratory and expiratory tubes.

7. A heated respiratory conduit as claimed in claim 6 wherein said heating element means and said low resistance electrical conducting means substantially extend the length of said inspiratory tube.

8. A heated respiratory conduit as claimed in claim 6 wherein a second heating element means is provided within said expiratory tube and extends substantially the full length of said expiratory tube, and a second low resistance electrical conducting means is provided within said expiratory tube, extending substantially the full length of said expiratory tube and connected at its proximal end to said second heating element means.

* * * * *